(12) United States Patent
Maniyam et al.

(10) Patent No.: US 9,565,804 B2
(45) Date of Patent: Feb. 14, 2017

(54) ENHANCING SECONDARY PHYTOCHEMICAL AND NUTRIENTS IN PLANTS AND PLANT PARTS

(76) Inventors: Anuradha Maniyam, Bangalore (IN); Balasubramanya Subbanarashiman, Bangalore (IN)

( * ) Notice: Subject to any disclaimer, the term of this patent is extended or adjusted under 35 U.S.C. 154(b) by 0 days.

(21) Appl. No.: 13/805,079

(22) PCT Filed: Jan. 31, 2011

(86) PCT No.: PCT/IN2011/000065
§ 371 (c)(1),
(2), (4) Date: Dec. 18, 2012

(87) PCT Pub. No.: WO2012/020420
PCT Pub. Date: Feb. 16, 2012

(65) Prior Publication Data
US 2013/0139282 A1    May 30, 2013

(30) Foreign Application Priority Data
Aug. 12, 2010 (IN) .......................... 2316/CHE/2010

(51) Int. Cl.
| | |
|---|---|
| *A01G 1/00* | (2006.01) |
| *A01N 59/16* | (2006.01) |
| *A01N 37/44* | (2006.01) |
| *A01N 65/22* | (2009.01) |
| *C05D 9/02* | (2006.01) |
| *C05F 11/00* | (2006.01) |
| *C05F 11/10* | (2006.01) |
| *C05G 3/00* | (2006.01) |

(52) U.S. Cl.
CPC .............. *A01G 1/001* (2013.01); *A01N 37/44* (2013.01); *A01N 59/16* (2013.01); *A01N 65/22* (2013.01); *C05D 9/02* (2013.01); *C05F 11/00* (2013.01); *C05F 11/10* (2013.01); *C05G 3/0064* (2013.01); *Y02E 50/343* (2013.01); *Y02W 30/47* (2015.05)

(58) Field of Classification Search
None
See application file for complete search history.

(56) References Cited

U.S. PATENT DOCUMENTS

| | | | | | |
|---|---|---|---|---|---|
| 4,455,161 | A | * | 6/1984 | Cohen ...................... | C05D 9/02 71/24 |
| 5,917,117 | A | * | 6/1999 | Ensley .................... | B09C 1/105 210/602 |
| 6,117,462 | A | * | 9/2000 | Ensley ..................... | A01G 7/06 426/615 |
| 6,324,785 | B1 | * | 12/2001 | Marrs ............................ | 75/711 |
| 2002/0132021 | A1 | * | 9/2002 | Raskin et al. ................ | 424/773 |
| 2003/0032605 | A1 | * | 2/2003 | Raad .................... | A61K 9/0019 514/28 |

FOREIGN PATENT DOCUMENTS

IN    WO 2008081472 A1 *  7/2008  ............. A61K 36/02

OTHER PUBLICATIONS

Markovic, I. et al., "Chemical Correlates of α-tocopherol (Vitamin E) Altered Malacosoma disstria Herbivory in *Fraxinus pennsylvania* var. *subintegerrinia*, Green Ash," Journal of Chemical Ecology, vol. 19, No. 6, 1993, p. 1205-1217.*
Schultz, "Schultze® All Purpose Slow-Release Plant Food," <http://schultz.infinitylawnandgarden.com/products/plant-food/granular/all-purpose> © 2013, p. 1-2.*
Dr. Lynette Morgan, "Article 5-4 Q's Nutrient Problems," <http://www.simplyhydro.com/nutrient_problems.htm>, published Mar. 22, 2009, p. 1-3.*

* cited by examiner

*Primary Examiner* — Tracy Vivlemore
*Assistant Examiner* — Monica Shin

(57) ABSTRACT

According to the invention, the object is achieved by providing all necessary conditions at optimum level to produce plant and plant parts having higher nutrients and secondary metabolites, when compared to normal plants or grown in tap water. Formulated solution containing balanced nutrients, higher levels of targeted nutrient, required pH, single or multiple eliciting factors, required concentrations of natural preservatives and maintained at required temperature and light facilitated to achieve the above object.

1 Claim, 3 Drawing Sheets

ENHANCING SECONDARY PHYTOCHEMICAL AND NUTRIENTS IN PLANTS AND PLANT PARTS

CROSS REFERENCES TO RELATED APPLICATIONS

This application claims priority from International PCT application No. PCT/IN2011/000065 filed on Jan. 31, 2011, which in turn claim priority from Indian patent application No. 2316/CHE/2010 filed on Aug. 12, 2010. Both applications are incorporated herein in its entirety by reference.

BACKGROUND

Field of Invention

This invention in general relates to plants and plant parts and in particular to enhancing secondary metabolites and nutrients in plants and plant parts.

Related Art

Plants often selectively absorb and accumulate micro and macro-nutrients from the place where it is growing such as soil, water, substrate, hydroponics and other sources. Lesser amount of micro and macro nutrients in sources/soil not only affects its accumulation in plant/plant parts but also affects both primary and secondary metabolism in plants.

Often deficiency in nutrients in the source is due to varied geographical conditions and prolonged usage of same source (for example, agricultural fields) without any replenishment causing changes in composition of nutrients in the soil. Such deficiency often results in lesser uptake of nutrients by the plants and plant parts. Such deficiency in uptake may result in various undesirable results. For example, such deficiency may result in lesser accumulation of desired nutrients in the fruits and vegetables produced by the plants/plant parts.

In general, plants have an ability to synthesize and accumulate secondary metabolites for its defence purposes, combat stress and aid pollination. These secondary metabolites synthesized and accumulated by plant parts are often used for medicinal, nutritive and cosmetic purposes. Often plants and plant parts are processed to extract these accumulated secondary metabolites. It is therefore desirable to produce the plant/plant part with higher nutrients and secondary metabolites in order increase the processing yield.

According to one aspect of the present invention, secondary metabolites in plants and/or in parts of plants are enhanced by inducing stress condition within the plant.

Another aspect of the present invention, nutrients and metabolites are simultaneously enhanced in a plants or plants part. In an embodiment of the present invention, secondary metabolites and or nutrients in a plant or plant parts are enhanced by growing the plants/plants part in a formulated solutions comprising of natural preservatives, target nutrients and elicitors individually or in combination.

According to yet another embodiment of the present invention, a product of the process is used as source of macro and micro-nutrient with higher levels of secondary metabolites for cosmetic, nutritional, pharmaceutical and therapeutic functions.

Further, in yet another aspect, nutrients are enhanced in plants and plant parts thereby providing natural and bio-available sources.

According to another aspect, the present invention provides cosmetic, nutritional, pharmaceutical and therapeutic products derived from natural source of phytochemicals and nutrients obtained from above technique.

According to another aspect of the present invention, metabolites and nutrients are extracted together or individually. Several aspects of the invention are described below with reference to examples for illustration. It should be understood that numerous specific details, relationships, and methods are set forth to provide a full understanding of the invention. One skilled in the relevant art, however, will readily recognize that the invention can be practiced without one or more of the specific details, or with other methods, etc. In other instances, well-known structures or operations are not shown in detail to avoid obscuring the features of the invention.

BRIEF DESCRIPTION OF THE DRAWINGS

The present invention will be described with reference to the following accompanying drawings.

DETAILED DESCRIPTION

Figure 1:
FIG. 1 shows freshly harvested roots of *Plectranthus barbatus* as described in an example embodiment.
Figure 2:
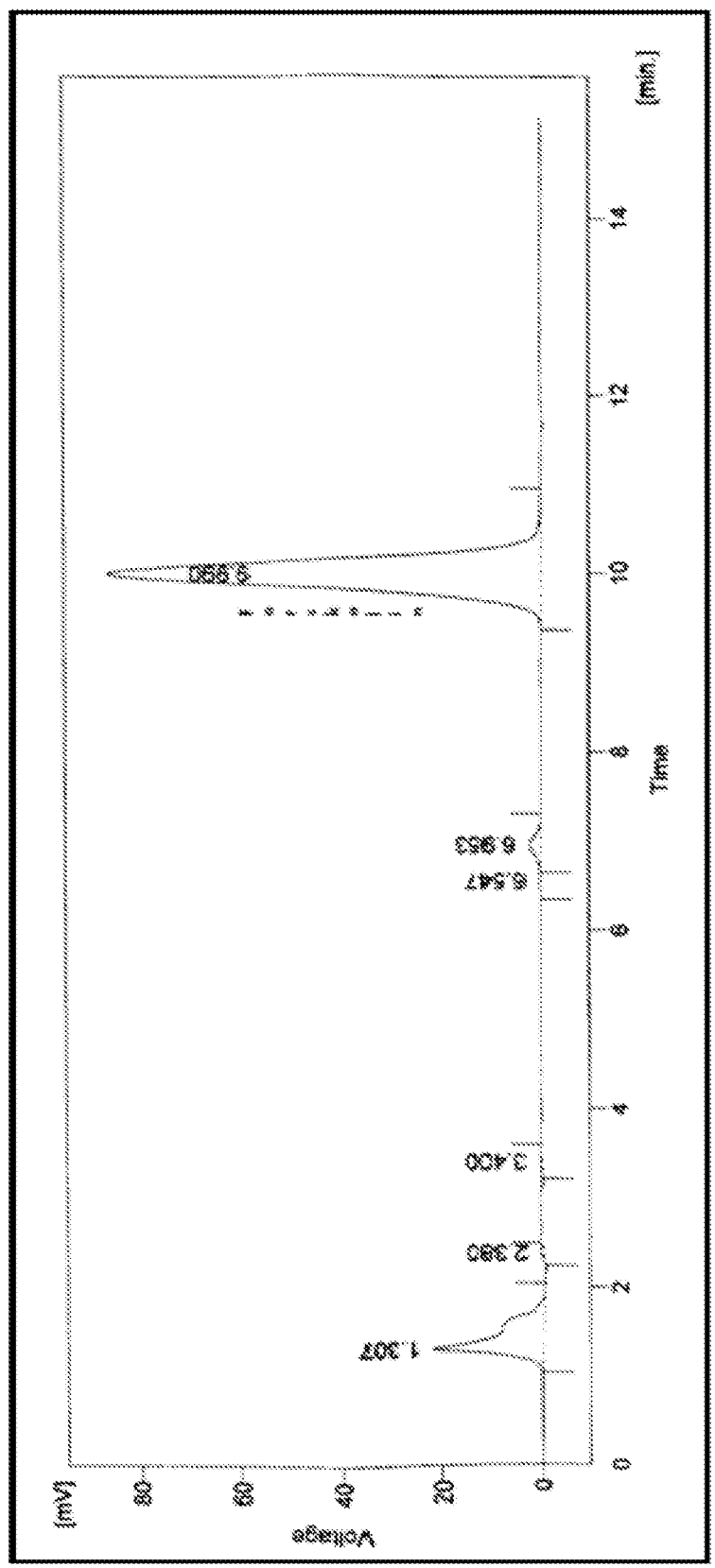
FIG. 2 Shows Chromatogram (HPLC) of forskolin standard (95%) in an example embodiment FIG. 3 Chromatogram (HPLC) of forskolin estimated in control dried roots *Plectranthus barbatus* after 7 days of treatment according to an example embodiment.
Figure 3:
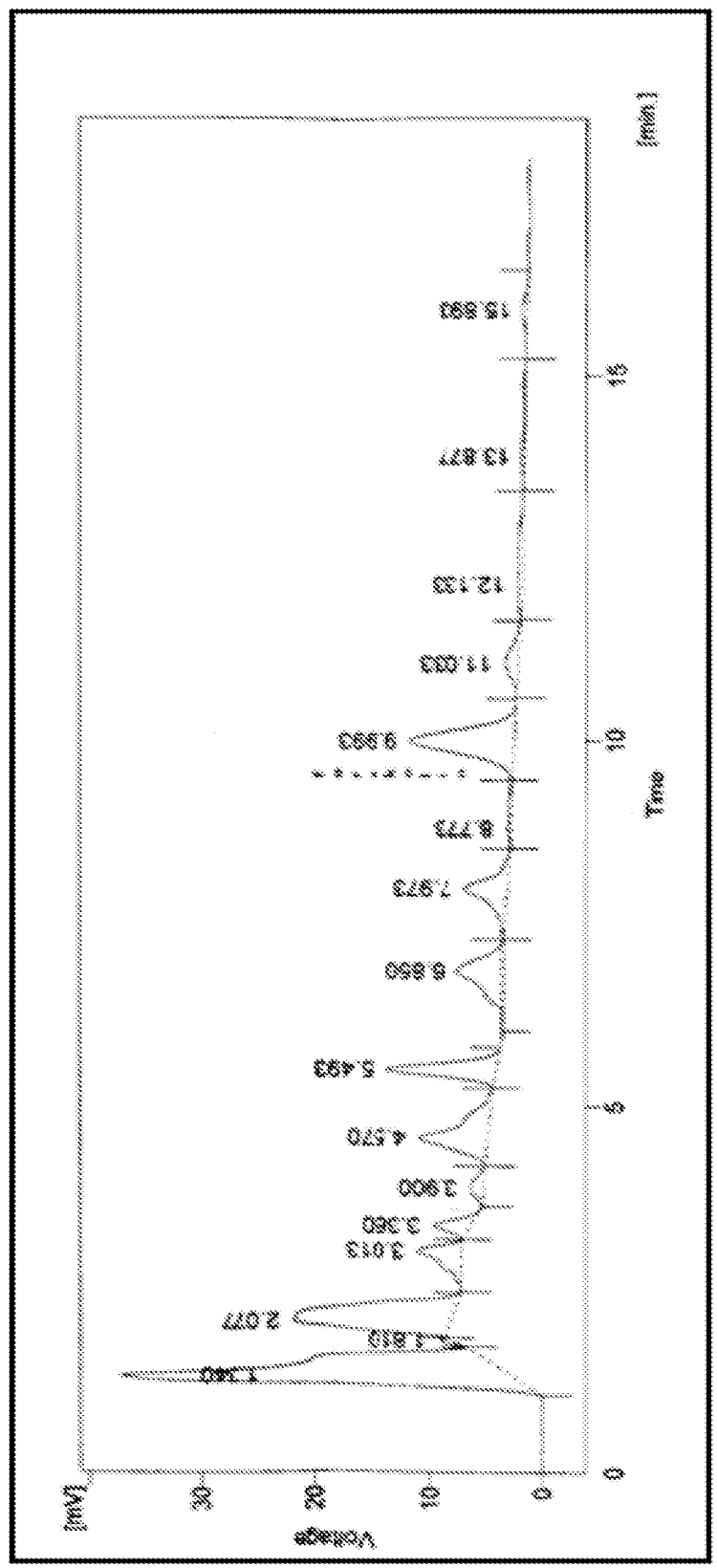

According to one embodiment of the present invention, the uptake of nutrients is increased to accumulate larger quantity of nutrients. Further, the synthesis is enhanced in the plant/plant parts to accumulate larger quantity of phytochemicals/Secondary Metabolites.

As a result, plants and plant parts of the present invention may be used/processed to obtain various nutrients, secondary metabolite (SM) and other compounds with a higher yield, less cost, higher safety and may be used widely for having long term health promoting or medicinal properties more so in prevention, management and curing of diseases. However, SM/phytochemicals in plants and plant parts are produced in very low quantities and also dependent on its physiological and developmental stages. Certain plants selectively absorb and accumulate nutrients from soil, which when consumed can contribute to the higher intake of nutrients. But geographical variations of nutrients content in soil will have a major role in the actual nutrient content in these plants.

Further certain plants are made to selectively absorb and accumulate nutrients from the formulated solutions that enable plants to contribute to the larger quantity of nutrients.

According to an aspect of the invention, the objective is achieved by growing the plant/plants parts in a formulated solution providing, all necessary conditions at optimum level to produce plant and plant parts having higher nutrients and secondary metabolites, when compared to normal plants or grown in tap water. Formulated solution contains balanced nutrients, higher levels of targeted nutrient, required pH, single or multiple eliciting factors, required concentrations of natural preservatives and maintained at required temperature and light at optimum level to produce plant and plant parts with larger quantity of nutrients and secondary metabolites, when compared to normal plants or grown in tap water. Thus, due to maintenance of light, temperature and pH level at a desired value, providing other nutrients for the overall growth and metabolism of the plant/plant part, the plant/plant parts are made to absorb the targeted nutrient in the formulated solution at a higher level there by accumulating the corresponding nutrients in the larger quantity. Further, the presence of natural preservatives in the formulated solution may prevent the growth and release of toxins by microbes which may further interfere with growth, metabolism and accumulation of targeted nutrients in the plants/plant parts grown in the formulated solution.

According to another aspect of the invention, the presence of the elicitors (otherwise absent in the other normal conditions in which plants are grown conventionally) in the formulated solution may trigger/cause enhanced synthesis in the plant/plant parts thereby may cause accumulation of larger quantity of phytochemicals/Secondary Metobolites in the plant part grown in the formulated solution. As a result, plants/plant parts are improved with increased amounts of nutrients and elevated levels of secondary metabolites simultaneously. The novelty of the entire process is using natural means to increase secondary metabolites and the product is unique having dual benefit of nutritional improvement with increased levels of secondary metabolites. Thus the present invention may be used for qualitatively improvising plants and plant parts in terms of secondary metabolites and nutrients.

According to one aspect, a process for naturally improving the cosmetic, dietary, preventive and therapeutic properties of plants and plant parts is disclosed. According to another aspect, the metabolism is manipulated under controlled conditions, there by not leaving any residual effects in the soil.

The description in the sections below illustrates method of growing plants and plant parts under controlled conditions, supported with a formulated solution, controlled temperature, pH and required photoperiod.

The description in the sections below illustrates the usage of formulated solution for supporting growth and metabolism which include micronutrients, macronutrients, elicitors, increased levels of targeted nutrients and natural preservatives.

The description in the sections below illustrates the elicitor used in the solution, which triggers the secondary metabolism thereby enhancing the levels of same in the plants and plant parts.

The description in the sections below illustrates targeted nutrient source which is provided in more available form, the lethal concentration of the nutrient is also described which affects the plant growth if used at higher levels.

The description in the sections below illustrates method of eliciting the secondary metabolite and the detection and identification of elicited content is described.

The description in the sections below illustrates extraction process of the plants and plant parts used to retain dual secondary metabolites and nutrients is described.

The description in the sections below illustrates the end product, which is having enhanced levels of secondary metabolites and nutrients when compared to normal plant, plant parts, roots, stems, leaves, twigs, inflorescence, buds, flowers, fruits and seeds, its powder and its extracts thereof.

The description in the sections below illustrates Post process data, which shows the presence of natural form of nutrients, elevated levels of secondary metabolites when compared normal plants and plant parts.

While the following description and examples are provided to certain embodiments of the invention, they are not intended to be limiting to the scope of the invention.

Several embodiments of the present invention are described below as examples merely for illustration and other extensions, applications, and usage of the present invention may be apparent to one skilled in the art. All such extensions, applications and usages are covered within the scope of the presentation invention.

The description is further made illustrating the manner in which formulated solution may be prepared for growing a plant/plant parts. Formulated solution may be prepared by mixing balanced nutrient solution, targeted nutrient solution, elicitor solution and preservative solutions in a required proportion. Accordingly, manner in which each such solution may be prepared is described below.

Example of Preparation of Balanced Nutrient Solution

In one embodiment, balanced nutrient solution of the present invention comprise macro nutrients at concentrations of at least 100 mg/l of nitrogen, sulfur, calcium, phosphorus, potassium and magnesium in the form of its salts, micronutrients at concentrations at least 0.025 mg/l of Iodine, boron, manganese, zinc, molybdenum copper cobalt and iron in form of its salts are dissolved separately one after the other and mixed to distilled or de-ionised water thoroughly. The stock solutions of the same were stored in a refrigerator at 10° C. and used as balanced nutrient solution for preparing formulated solution. The stock solution may be discarded if there is precipitate or contamination.

Example of Preparation of Targeted Nutrient Solution:

There are different nutrient sources among them some are water soluble, non-water soluble, some exist in the form of salts, some are in chelated forms and some are having different valances. For example chromium exists in trivalent and hexavalent form where in the former is non-toxic and later is toxic. The uptake of nutrients depends on all above said objects whose affect is seen in form of health problems associated with diets deficient in such nutrient. Also local variations in nutrients in regular growth environment such as soil, has led to many levels of nutrients deficiencies.

In one embodiment, the form of the targeted nutrient source is converted to facilitate the higher absorption by the plant/plant parts.

For example, chromium targeted solution is prepared by converting chromium nitrate to chromium EDTA as described below.

Preparation of Chromium EDTA was done where in chromium nitrate (8.1 gms) was weighed and dissolved in 25 ml of distilled water. 10 gms of sodium EDTA was weighed and boiled to dissolve in 60 ml of distilled water. pH of the Sodium EDTA solution is adjusted to 5.5-5.6 with 70% sodium bicarbonate solution. The solution are mixed thoroughly and made up to 100 ml by adding distilled water. Required concentrations were added to the balanced nutrient solution.

Required concentration in one embodiment is selected to be below a (lethal) concentration. For example, chromium is used at 4 gm/liter.

Elicitor: An elicitor is an object that triggers the production of phytochemicals, as a defense response to stress. Plants tend to accumulate secondary metabolites in specific cells, at specific stage and very often in response to environmental stresses. In the event of attack of pathogens, pests, herbivores or any other biotic and abiotic factors, plants respond by activating a range of defense mechanisms which includes induction of biosynthesis of secondary metabolites as phytoalexins.

Earlier the term elicitor was used for compounds that stimulate production of phytoalexins. It is possible that plants and plant parts accumulate more secondary metabolites when they are subjected to certain biotic and abiotic stresses. Now it is commonly used for agents that initiate any type of plant defense be it biotic or abiotic in origin. In present invention yield of the SM/phytochemicals were increased by subjecting the selected plant or plant parts to elicitor/s be it abiotic and biotic. In this invention the targeted nutrient at higher concentrations also behave as elicitor and contribute to the increase in SM/phytochemical and at the same time accumulate thus enhancing its nutritional properties.

Example of Preparation of Elicitor Solution:

Potatoes (200 gms) were cut into slices and boiled with 200 ml of distilled water and then filtered through muslin cloth. Twenty grams of dextrose was added to the filtrate and the volume was made up to 1000 ml. The pH of the medium was adjusted to 6.5. Into each 250 ml conical flask 50 ml of the media is dispensed and autoclaved. Loop full of *Aspergillus niger* inoculum grown on solid medium was inoculated into medium. The flasks were incubated and allowed to grow. After 20 days, during sporulation flasks with the cultures were autoclaved. The fungal mat was separated by filtration and then washed several times with distilled water. Aqueous extract was made by homogenizing the mat in a mortar and pestle using acid washed neutralized sand. The homogenized mat was filtered through muslin cloth to obtain mat extract. Required concentrations of mat extracts and mat filtrates were added to the balanced nutrient solution.

Example of Preparation of Preservative Solutions:

1% Rosemary Extract was added to the formulated solution.

Example of Preparation of Formulated Solution:

Solutions of example 1, 2, 3 and 4 were mixed at required concentration based on the plant and plant parts selected and this becomes the formulated solution of the present invention.

Example of Growing Plant/Plant Parts in the Formulated Solution:

Intact or freshly harvested plant parts or plants are fed/grown with/in formulated solution described above and the concentrations and duration of the same is adjusted to the type of plant or plant part selected and also to the targeted nutrient and phytochemicals to be enhanced. One example is described below.

Freshly harvested plant along with roots of *Plectranthus barbatus* was subjected to thorough washing to remove soil and dust. The washed roots were surface sterilized using 1% Teepol solution. 800 gms of intact roots were kept in containers immersed in formulated solutions leaving some portions of plants and plant parts above the solution. The entire process was carried under controlled (pH, temperature, light, preservative) and clean conditions. Required temperature and light was maintained at to induce growth and metabolism. The formulated solution was changed every 12 hours and growth and metabolism process was carried out for 3 hrs to 10 days. The roots of the plant thus grown in the formulated solution is then harvested, thoroughly washed, dried and powdered to suitable mesh.

Example of Extraction of Nutrients and SM/phytochemicals

The plants and extract comprises of active ingredient of the plant preserved in water or any other solvents. In the present embodiment active ingredient means targeted nutrient, as well as enhanced phytochemical. The following example further illustrates extracting nutrient/s and SM together.

The improvised and fully dried roots were pulverized to powder and further subjected to extraction with ethanol at 70° C. for two hours. The ethanolic extract was filtered and concentrated in vacuum.

Additional Example of Extracting Phytochemical

The improvised and fully dried roots were pulverized to powder and further subjected to extraction with ethyl acetate at 70° C. for two hours. The ethyl acetate extract was filtered and concentrated in vacuum.

Further Example of Extracting Nutrient

The improvised and fully dried roots were pulverized to powder and further subjected to extraction with water at 70° C. for two hours. The extract was filtered and concentrated in vacuum. The extract was then subjected to detection and quantified using ICP-OES for the targeted nutrient which has accumulated several fold when compared to control.

Detection and Estimation of Forskolin

The plants, plant parts and extract were assayed for forskolin content by High pressure liquid chromatography (HPLC)

Standard preparation: About 25 mg of standard forskolin was weighed accurately into a 25 ml volumetric flask, dissolved and diluted to volume with methanol and mixed well.

Sample preparation: One gram of sample was weighed into a 100 ml flask, 50 ml of methanol was added and refluxed for 30 minutes. The process was repeated with 3×50 ml of methanol. All the methanol extracts were combined and diluted to 250 ml with methanol, mixed and filtered through Whatman No. 42 to get a clear solution.

Mobile phase: Hexane, ethylacetate and methylene chloride were mixed in the proportion of 70:20:10 and degassed.

Chromatographic system: The liquid chromatograph (Shimadzu Corporation, Kyoto, Japan) was equipped with a 210 nm UV detector and C18 column (250×4.6 mm: M/s Spinco Biotech Pvt. Ltd., Bangalore, India). The mobile phase was pumped at the rate of 0.8 ml/min with a back pressure of 200 psi. The injector and the detector were flushed with the mobile phase. The refractive index of the detector was set at 4× and the potentiometer chart speed was set at 0.5 cm/min.

The column was equilibrated for half an hour. The flow rate was about 1.0 ml per minute. The standard preparation was chromatographed and the peak response for forskolin was recorded. Equal volumes of (10 μl) of the standard preparation and sample preparation were injected separately. Recorded the chromatograms and measured the responses for the peak corresponding to forskolin.

The said plants, plant parts and extract was further subjected to detection and quantified using inductively Coupled Plasma—Optically Emission Spectrophotometer (ICP-OES) for the targeted nutrient which has accumulated several fold when compared to control.

Preparation of standards: The working standard solutions were prepared in the range of 0 to 1.5 ppm (0, 0.5, 1, and 1.5 ppm) by diluting appropriately the standard chromium solution with dilute nitric acid.

Preparation of Sample: Weighed about 3 grams of the sample into a 30 ml silica crucible. Heated first over a low Bunsen flame to volatilize the organic matter until no more smoke came out from the material. Then the crucible was transferred to as muffle furnace having temperature of 550° C. and kept for 5-6 hours for complete ashing. Removed the crucible from the furnace and allowed it to cool. The contents of the crucible were transferred quantitatively into a 150 ml beaker with help of distilled water using water jet. To the above 10 ml of dilute nitric acid and 10 ml of dilute hydrochloric, acid was added. Boiled the contents for about 10-15 minutes and allowed it to cool. If any black particles were found, it indicated the incomplete ashing. The whole process was repeated with fresh sample keeping for more time in furnace for ashing. The cooled solution was made up to a known volume with help of distilled water. Performed a blank using all reagents except sample and apply proper correction for test concentration.

Procedure: AAS (M/s GBC Scientific Equipment, Australia, model 932AA) and ICP-OES (M/s Horiba Scientific, USA, Jobin Yvon, Series 24) was switched on as per the work instruction and allowed for the stabilization. The instruments were calibrated by aspirating the known standard solutions. The test solutions were also aspirated and noted down the readings in ppm.

While various embodiments of the present invention have been described above, it should be understood that they have been presented by way of example only, and not limitation. Thus, the breadth and scope of the present invention should not be limited by any of the above described exemplary embodiments, but should be defined only in accordance with the following claims and their equivalents.

What is claimed is:

1. A method comprising:

preparing a formulated solution comprising an elicitor, a chromium EDTA in a organic form and an active agent;

harvesting an unit of a *Plectranthus barbatus* comprising a first quantity of a forskolin and a substantially zero quantity of a chromium, the *Plectranthus barbatus* not requiring the chromium for active metabolism;

processing the *Plectranthus barbatus* with the formulated solution for 3 hours to 10 days to form a processed *Plectranthus barbatus* comprising a second quantity of forskolin and a third quantity of the chromium in an organic form, the second quantity being greater than the first quantity, the third quantity being adequate for extraction;

simultaneously extracting substantially the second quantity of the forskolin and the third quantity of the chromium in organic form from the unit of the processed *Plectranthus barbatus*; and forming a pharmaceutical composition comprising the chromium and the forskolin.

* * * * *